United States Patent [19]
Gilligan et al.

[11] Patent Number: 5,526,831
[45] Date of Patent: Jun. 18, 1996

[54] DENTAL FLOSS MANUFACTURING PROCESS AND PRODUCT

[75] Inventors: Sean G. Gilligan, Kilcullen; Dermot T. Freeman, Killiney, both of Ireland; Larry J. Oliphant, Swisher; Jeffrey S. Meessmann, Iowa City, both of Iowa; Patrick J. Hanley, South San Francisco, Calif.; Gerald S. Szczech, Iowa City, Iowa

[73] Assignee: Gillette Canada, Inc., Canada

[21] Appl. No.: 249,503

[22] Filed: May 26, 1994

Related U.S. Application Data

[63] Continuation-in-part of Ser. No. 151,707, Nov. 12, 1993, abandoned.

[51] Int. Cl.$^6$ ........................................... A61C 15/00
[52] U.S. Cl. .................. 132/321; 242/534.2; 364/470
[58] Field of Search .................................. 132/321, 329; 242/36, 534.2; 364/469, 470

[56] References Cited

U.S. PATENT DOCUMENTS

| | | |
|---|---|---|
| 174,619 | 3/1876 | Clark, Jr. . |
| 290,678 | 12/1883 | Gourdiat . |
| 660,943 | 10/1900 | Bavermeister . |
| 2,667,443 | 1/1954 | Ashton . |
| 2,700,636 | 1/1955 | Ashton . |
| 2,748,781 | 6/1956 | Collat . |
| 3,412,192 | 11/1968 | Clapson . |
| 3,492,131 | 1/1970 | Schlatter . |
| 3,615,671 | 10/1971 | Shoaf et al. . |
| 3,642,491 | 2/1972 | Schlatter . |
| 3,699,979 | 10/1972 | Muhler et al. . |
| 3,771,536 | 11/1973 | Dragan . |
| 3,789,858 | 2/1974 | Pesce . |
| 3,800,046 | 3/1974 | Schlatter . |
| 3,828,419 | 8/1974 | Wanner . |
| 3,830,246 | 8/1974 | Gillings . |
| 3,837,351 | 9/1974 | Thornton . |
| 3,838,702 | 10/1974 | Standish et al. . |
| 3,896,824 | 7/1975 | Thorton . |
| 3,897,795 | 8/1975 | Engel . |
| 3,906,757 | 9/1975 | Arimoto et al. . |
| 3,943,949 | 3/1976 | Ashton et al. . |

(List continued on next page.)

FOREIGN PATENT DOCUMENTS

| | | |
|---|---|---|
| 0080440 | 6/1983 | European Pat. Off. . |
| 0335466 | 10/1989 | European Pat. Off. . |
| 2216803 | 10/1989 | United Kingdom . |

*Primary Examiner*—Todd E. Manahan
*Attorney, Agent, or Firm*—William B. Walker

[57] ABSTRACT

A continuous process for manufacturing a continuous floss brush comprises steps of first applying a polymer solution at a repeated preselected distance interval to a continuous length of floss yarn under tension and solidifying the polymer while the floss yarn is under tension to produce a continuous floss product of yarn sections which stretch under slight tension separated by thread sections which do not significantly stretch under tension. The floss yarn is treated to expand the yarn sections to form brush sections. The passage of a predetermined number of segments comprising thread and brush portions is determined while the continuous floss brush is under substantially zero tension using a optical detector. Finally, a length of the continuous floss segments containing the predetermined number of segments comprising thread and brush portions is cut for packaging. Preferably, a dye marker is applied to at least a portion of the thread portion, whereby the accuracy of the optical detection of the thread portions of the continuous floss brush is increased. The yarn is a nylon yarn, and the yarn sections are expanded by treatment with heat and water vapor when under zero tension to yield a product with a highly expanded brush portion which is stretched under slight tension. The floss brush product comprises a continuous length of floss having segments comprising alternating portions of yarn sections which stretch under slight tension separated by thread sections which do not significantly stretch under tension, at least a portion of each thread section being preferably marked with a dye.

15 Claims, 2 Drawing Sheets

U.S. PATENT DOCUMENTS

| | | |
|---|---|---|
| 3,953,962 | 5/1976 | Breen et al. . |
| 3,972,214 | 8/1976 | Jagersberger . |
| 3,991,704 | 11/1976 | Hulstein et al. . |
| 4,000,964 | 1/1977 | Newton . |
| 4,008,727 | 2/1977 | Thornton . |
| 4,013,435 | 3/1977 | Kane et al. . |
| 4,020,194 | 4/1977 | McIntyre et al. . |
| 4,029,113 | 6/1977 | Guyton . |
| 4,033,365 | 7/1977 | Klepak et al. . |
| 4,047,271 | 9/1977 | Paterson et al. . |
| 4,071,615 | 1/1978 | Barth . |
| 4,073,260 | 2/1978 | Bosworth et al. . |
| 4,073,998 | 2/1978 | O'Connor . |
| 4,096,611 | 6/1978 | Heyner . |
| 4,142,538 | 3/1979 | Thornton . |
| 4,153,961 | 5/1979 | Cleveland . |
| 4,158,976 | 6/1979 | Ditges . |
| 4,184,316 | 1/1980 | Griset, Jr. . |
| 4,291,017 | 9/1981 | Beierle et al. . |
| 4,350,311 | 9/1982 | Pokhodnya et al. . |
| 4,414,990 | 11/1983 | Yost . |
| 4,415,978 | 11/1983 | Craemer et al. .......................... 364/470 |
| 4,530,855 | 7/1985 | Youngkeit . |
| 4,548,219 | 11/1985 | Newman et al. . |
| 4,605,573 | 8/1986 | Deeg et al. . |
| 4,627,975 | 12/1986 | Lynch . |
| 4,638,823 | 1/1987 | Newman et al. . |
| 4,737,904 | 4/1988 | Ominato . |
| 4,817,643 | 4/1989 | Olson . |
| 4,858,844 | 8/1989 | Stenqvist ............................. 242/534.2 |
| 4,908,153 | 3/1990 | Kossmann et al. . |
| 4,911,927 | 3/1990 | Hill et al. . |
| 4,919,869 | 4/1990 | Zatkulak et al. . |
| 4,932,092 | 6/1990 | Yoshida . |
| 4,941,487 | 7/1990 | Van Beneden . |
| 4,952,392 | 8/1990 | Thame . |
| 4,974,615 | 12/1990 | Doundoulakis . |
| 4,986,288 | 1/1991 | Kent et al. . |
| 4,996,056 | 2/1991 | Blass . |
| 4,998,978 | 3/1991 | Varum . |
| 5,033,488 | 7/1991 | Curtis et al. . |
| 5,042,343 | 8/1991 | Boyadjian . |
| 5,063,948 | 11/1991 | Lloyd . |
| 5,141,780 | 8/1992 | Hackler et al. . |
| 5,163,008 | 11/1992 | Gerber at al. ........................... 364/470 |
| 5,284,169 | 2/1994 | Gilligan et al. . |
| 5,320,873 | 6/1994 | McClain et al. . |
| 5,395,647 | 3/1995 | Krug . |

DENTAL FLOSS MANUFACTURING PROCESS AND PRODUCT

RELATIONSHIP TO APPLICATION

This application is a continuation-in-part of application Ser. No. 08/151,707 filed Nov. 12, 1993, now abandoned. Another commonly assigned application relating to floss having a brush portion is Ser. No. 07/832,151 filed Feb. 6, 1992 now U.S. Pat. No. 5,353,820.

BACKGROUND OF THE INVENTION

Tooth decay and dental disease can be caused by bacterial action resulting from the formation of plaque about the teeth and/or the entrapment of food particles between the teeth and interstices therebetween. The removal of plaque and entrapped food particles reduces the incidence of caries, gingivitis, and mouth odors as well as generally improving oral hygiene. Conventional brushing has been found to be inadequate for removing all entrapped food particles and plaque. To supplement brushing, dental flosses and tapes have been recommended. The term "dental floss", as used herein, is defined to include both dental flosses, dental tapes and any similar article.

To improve the effectiveness and convenience of dental flosses, dental flosses combining a thin "floss" portion and a thickened "brush" portion, together with a threader have been developed. The brush portion, when drawn between tooth surfaces, has been found to provide an improved cleaning action which removes materials left by the floss portion, when used alone. The combination provides a substantially superior cleaning action. Such a device is described in U.S. Pat. No. 4,008,727, for example. The complexity of this product requires that each floss segment be individually manufactured and that the product be packaged as bundles of the individual, separate floss articles.

A continuous yarn having brush segments separated by thinner segments is disclosed in U.S. Pat. Nos. 4,008,727 and 4,142,538. However, products formed using conventional textured nylon yarns and previously developed manufacturing processes were not satisfactory. Manufacture of brush floss products of this type involves applying a polymer solution to the yarn. The solvent is then selectively evaporated from the thinned segment portion while avoiding solvent evaporation from the brush portion, the yarn being maintained under high tension during this procedure. The solvent in the brush portion is then removed while the yarn is relaxed, that is, under low or no tension. Thin yarn products of most texturizing processes were found to be too weak to be placed under the high tension required for forming the desired thin section. Furthermore, the polymer impregnated brush portion did not regain its original bulk and texture when the tension was relaxed prior to solvent removal from the brush portion.

An improved floss brush product and processes for manufacturing it which overcome these deficiencies are described in U.S. Pat. No. 5,284,169. The entire contents of the above application is hereby incorporated by reference.

In manufacturing these continuous floss brushes, measurement of actual floss length and/or number of floss units for packaging presents a difficult problem because the brush portion is highly expanded and stretches when placed under any tension. Therefore, the lengths of floss segments may differ depending upon the tension under which they are measured and the amount of expansion or bulking during manufacture. The segment lengths are thus not precisely reproducible, and accordingly, traditional methods for automatically measuring length and/or number of use segments based directly or indirectly on length measurements are not effective with this product. For the same reason, locating of suitable points to cut lengths of floss for packaging and use based on length presents a problem.

OBJECTS AND SUMMARY OF THE INVENTION

It is one object of this invention to provide an improved process for manufacturing accurate lengths and segment numbers of floss brush products.

It is another object of this invention to provide an improved continuous floss product of segments comprising brush and thread portions, the boundary between floss segments being identified with a marker.

In summary, the continuous process of this invention for manufacturing a continuous length of floss brush segments comprises steps of first applying a polymer solution at a repeated preselected distance interval to a continuous length of floss yarn and solidifying the polymer while the floss yarn is under tension to produce a continuous floss product of yarn sections which are expanded, separated by thinner thread sections having a polymer coating. The floss yarn is treated to expand the yarn sections further to form brush sections. The passage of a predetermined number of segments, comprising thread and brush sections, is determined using a detector while the continuous floss brush is under substantially zero tension. Finally a length of the continuous floss brush containing the predetermined number of segments is cut and packaged.

A polymer solution may be applied to at least the yarn sections once the polymer on the thread sections has solidified and before treating the floss yarn to expand the yarn sections.

The detector may be an optical detector.

Preferably, a dye marker is applied to at least a portion of the thread portion, whereby the accuracy of the optical detection of the thread portions of the continuous floss brush is increased. The yarn may be a nylon yarn, and the yarn sections may be expanded by treatment with heat and water vapor when the yarn sections are under substantially zero tension, to yield a product with a highly expanded brush portion which stretches under slight tension.

In summary, the floss brush product of this invention comprises a continuous length of floss segments having alternating portions of yarn sections which are expanded, separated by thread sections, at least a portion of each segment being marked with a dye.

Preferably, the yarn is a reverse twisted, high tenacity nylon yarn comprising at least two thread sections having diameters, in their relaxed state, of less than 0.5 mm, the thread sections being separated by a floss brush section integral therewith of yarn having a diameter of 1 to 3 mm in its relaxed state, a diameter of from 0.5 to 1.0 under a tension of 0.05N, the floss brush having a breaking strength of at least 5N. Optimally, the reverse twisted high tenacity nylon yarn has a breaking strength of at least 20N. The thread sections have diameters, in their relaxed state, of less than 50 percent of the diameter of relaxed, uncoated yarn from which they were formed; and the floss brush section has, in its relaxed state, at least 100 percent of the original diameter of relaxed, uncoated yarn from which it was formed. The brush section should easily stretch under tension, each floss brush section having a diameter under a tension of 0.05N of at least 60 percent of relaxed uncoated yarn from which it was formed.

DETAILED DESCRIPTION OF THE INVENTION

The elongate teeth cleaning article of this invention provides the combined functions of an interproximal brush and floss. In the representation shown in FIG. 1, each segment of the polymer coated thin floss brush 2 comprises a brush section or portion 4 positioned between terminal thread portions 6 and 8 integral therewith. The brush portion, when under low tension, is relaxed, expanded or bulked yarn, suitable for cleaning between the teeth in a brushing action, pulling the floss backward and forward across tooth and gingiva surfaces. The cavities in the surface of the brush portion capture and remove food, bacteria and other materials on the tooth and gum surfaces. Under tension, the brush portion stretches to become a thread, suitable for the upward and downward scraping motion along the opposed tooth surfaces and facilitates easier insertion between interstitial spaces. When tension is relaxed, the brush portion returns to its expanded configuration.

Figure 1:
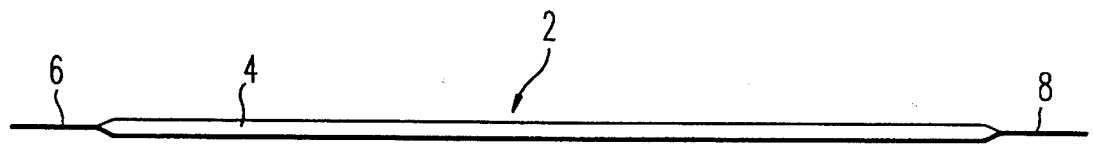
FIG. 1 is a representation of the relaxed dental floss brush of this invention.
Figure 2:
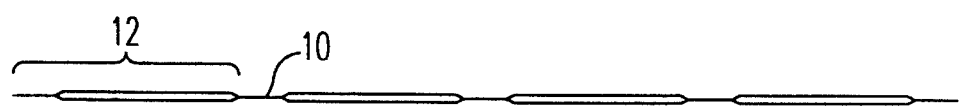
FIG. 2 is a representation of a continuous length of relaxed, connected dental floss brushes of this invention.

The thin floss brush 2 is manufactured in a continuous length having repeating segments, each segment comprising thread and brush portions, one preferred configuration of which is shown in FIG. 2. By severing the thread portion 10 separating a terminal thread and brush portion 12, a floss segment corresponding to FIG. 1 is obtained. This continuous length of floss segments is suitable for dispensing from a spool in a conventional floss dispenser.

It will be readily evident to a person skilled in the art that the thread section can be lengthened to yield a traditional thread floss portion. It will also be readily evident that terminal thread portions can have coating thicknesses sufficient to provide a "threader" function suitable for insertion between interproximal surfaces and under tooth reconstructions such as bridges. One such floss is described in commonly assigned, copending application Ser. No. 07/832,151 filed Feb. 6, 1992, the entire contents of which are hereby incorporated by reference. All of these variations are intended to be included within the scope of this invention.

Figure 3:
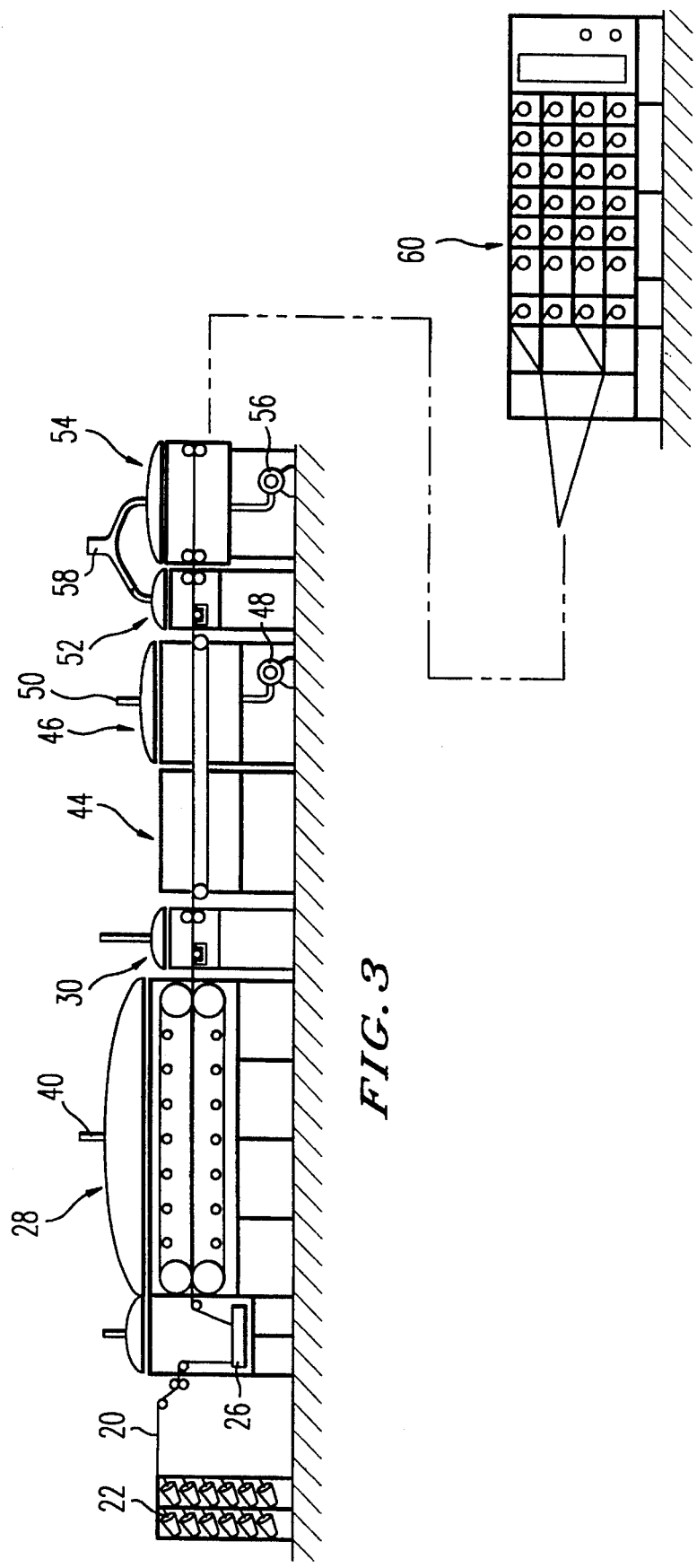
FIG. 3 is a schematic representation of one system for producing a continuous length of connected dental floss brushes of this invention.

FIG. 3 is a schematic representation of one system for producing a continuous length of connected dental floss brushes of this invention. The dental floss brush produced by this process comprises alternating sequences of thread portions and floss brush portions. The process comprises the following steps. At least the thread portions of a reverse twisted high tenacity nylon yarn are coated under tension with a solution of polymer in a volatile solvent, the polymer being selected from the group consisting of nylon, polyurethane and mixtures thereof. The thread portions of the yarn are heated, vaporizing solvent therefrom while the yarn is maintained under a tension of from 0.15 to 1N. The brush portions of the yarn are exposed to steam while the yarn is under zero tension until the brush portions of the yarn have regained at least 100 and preferably at least 220 percent of the diameter of the uncoated, relaxed yarn. The brush portions of the yarn are then heated, removing solvent therefrom while the yarn is held under zero tension to form a floss brush product.

In the embodiment shown in FIG. 3, only the thread portions of a reverse twisted high tenacity nylon yarn are coated with a solution of polymer in a volatile solvent in the initial step, the polymer being selected from the group consisting of nylon, polyurethane and mixtures thereof. The yarn is heated, vaporizing solvent therefrom while the yarn is maintained under a tension of from 0.15 to 1N. Then at least the brush portions of the yarn are coated with a solution of polymer in a volatile solvent, the polymer being selected from the group consisting of nylon, polyurethane and mixtures thereof. The yarn is then exposed to steam while the yarn is under zero tension until the brush portions of the yarn have regained at least 100 percent and preferably until the brush has bulked or expanded to at least 220 percent of the original diameter of the uncoated, relaxed yarn. The yarn is then heated, removing solvent therefrom while the yarn is under zero tension to form a floss brush product.

In the preferred embodiment, yarn 20 is drawn from yarn packages (spools or cones) which are mounted on a creel 22. Yarn 20 is pulled through the polymer coating and dye applicator 26. In coating and dye applicator, a polymer and dye solution in a volatile solvent is applied only to the short sections of the yarn which are intended to be thread portions of the final product. The polymer is applied to the yarn while the tension is increased, effecting liquid penetration of the yarn while avoiding excessive liquid pickup.

The coated yarn, under tension, is then transported through heater and solvent vaporizer unit 28. This system is a conventional tunnel drier which applies heat to the yarn, venting solvent vapors from an exhaust manifold through the exhaust conduit 40. The temperature in the tunnel drier is preferably within the range of from 90° to 120° C.

The yarn is then passed through a coating bath 30 where a second polymer solution is applied. The polymer is applied to the yarn while it is under tension, effecting liquid penetration of the yarn while avoiding excessive liquid pickup.

The yarn is then passed under relaxed conditions (i.e., low or zero tension) into a steam treatment chamber 44. When the yarn tension is relaxed after emerging from the coating bath 30, these undried portions partially contract to a partially bulked configuration. In steam chamber 44, the brush portions are exposed to a mixture of steam and gas having a temperature of 130° C. and a water vapor content of 65% (v/v) until the brush portions contract and substantially regain or preferably exceed the original puffiness and bulked condition of the initial uncoated, relaxed yarn. This is usually achieved by a treatment of 3 seconds and longer, depending upon the nature and level of coating. The steam/gas mixture is preferably a steam/air mixture having a temperature of 130° C. and a water content of 65% (v/v).

The rebulked, steam-treated floss is then passed into roller driven drying chamber 46. The residual liquid (solvent and water) is evaporated by conduction and convection heat transfer using heated air having a temperature within the range of from 150° to 200° C. and a flow rate of 150 to 300 cfm. Air is supplied through manifold 50 and vapors are removed through exhaust system 48.

The continuous length of floss brush can be collected on reels as an unwaxed floss product at this stage.

Optionally, for producing a waxed floss brush, the solvent-free floss is passed through a wax coating bath 52 where a low melting wax coating is applied at an elevated temperature. The excess wax coating is removed by passing the floss brush between squeeze rollers, and the continuous length of floss brush is passed into the refrigeration or cooling station 54. Passing through a gas stream produced by blower 56, solvents are evaporated and the vapors removed through exhaust manifold 58. The wax coated product is then collected on reels (spools or cones) in the collecting station 60.

The floss brush is then rewound from the spools or cones onto conventional individual dispenser spools using the optical counting system of this invention.

Most textured nylon yarns were found to lack the tensile strength required for this process. The products of most bulking processes lack the aesthetic appeal required for this product, i.e., wild strands, broken filaments, etc. False twist texturizing provides the most satisfactory aesthetic appearance. For making a thin floss brush product, use of yarn having a lower decitex is required without sacrificing strength.

False twisting gave an acceptable aesthetic product, but strength was found to be limiting. During texturizing, the yarn is subjected to extreme heat, reducing its strength. For yarns prepared by twisting together an uneven number of ends (such as five 2×2×1), often one end failed under tension, reducing the overall strength of the yarn. We found that by controlling the heat to avoid damaging extremes, a false twisted product having the required strength could be obtained.

The steaming process increased bulk of the yarn, yielding a product which slips easily between teeth under tension and which bulks up to be used either as a floss, cleaning by scraping up and down, or by linear movement as a brush. The bulked portion is easier on the gums. The product can accept liquid or solid flavoring materials because of its open mesh structure and increased surface area over regular floss. This provides a product with a more lasting flavor and increased customer appeal.

Reverse or false twisted, high tenacity nylon yarn having a breaking strength of at least above 5N, preferably above 20N and optimally above 35N was found to be satisfactory. These yarns are formed by first texturizing a high tenacity nylon yarn using a conventional pin-twisting process, using only sufficient heat required for the texturizing and avoiding temperatures which will significantly damage the yarn and its filaments and reduce their strength. Left and right pin-twisted strands are then combined to form the final reverse-twisted, textured yarn product. A suitable yarn is available from Chapman Fraser & Co. Ltd. Thurmaston, Leicester, England.

The coating and dye indicator polymer solution applied in coating bath 26 can be a solution or emulsion of a nylon, polyurethane or mixtures thereof. It is preferably a solution of from 5 to 30 wt. % urethane polymer in a volatile solvent. Preferred volatile solvents include a mixture comprising a major amount of a lower alcohol, preferable having from 1 to 3 carbon atoms, and a minor amount of an aromatic hydrocarbon. An optimum dye indicator and polymer solution has the following composition.

| DYE AND POLYMER COATING COMPOSITION | |
|---|---|
| Component | Amount, wt. % |
| Polyurethane aliphatic prepolymer[a] | 15.0 |
| Isopropyl alcohol | 58.5 |
| Methanol | 25.0 |
| Toluene | 1.5 |
| FD&C Blue #1[b] | 0.5 mgms/mL |

[a]SPENLITE L90-20A, Reichhold Chemicals, Inc.
[b]No. 5601 FD&C Blue #1, Warner Jenkinson The polymer solution applied in the coating bath 30 can be a solution or suspension of nylon, polyurethane or mixtures thereof in a volatile solvent. It is preferably a solution of from 5 to 30 wt. % urethane polymer in an aqueous solvent mixture comprising a major portion of water and a minor portion of organic solvent. The aqueous solvent mixture is optimally at least 75 wt. % water and less than 15 wt. % organic solvent. One optimum polymer solution which can be used in the coating bath 30 is as follows:

| POLYMER COATING COMPOSITION | |
|---|---|
| Component | Amount, wt. % |
| Polyurethane, water dispensable[a] | 11.2 |
| N-methyl-2-pyrrolidone | 5.6 |
| Triethylamine | 1.05 |
| Water | 82.15 |

[a]SPENSOL L54, Reichhold Chemicals, Inc.

Application of conventional microcrystalline waxes or polyethylene glycol waxes to nylon yarns clog the spaces of the yarn and make it ineffective for use as a brush. We have discovered, however, that low melting, non-tacky waxes such as heated liquid polyethylene glycol esters of beeswax can be use to coat such yarns, and if the excess is removed before cooling, only the individual filaments of the yarn are coated and most of the original yarn texture and cleaning ability is retained.

The heated polyethylene glycol esters of beeswax have a low melting temperature, usually within the range of from 65° to 70° C., and are mutually soluble with flavor oils. They therefore provide a suitable vehicle for applying flavoring to the floss brush. They also function as emulsifiers and surfactants and can be combined with alkanolic or aqueous solutions of sweeteners such as saccharine, cyclamates or xylitol and with lubricants such as silicone oils. Preferred low melting wax coating compositions are esters of polyethylene glycols having an average molecular weight of 300 and beeswax. A preferred unflavored coating composition is shown in the following table.

| UNFLAVORED WAX COATING COMPOSITION | |
|---|---|
| Component | Amount, wt. % |
| Polyethylene glycol ester of beeswax[a] | 50.0 |
| Silicone oil lubricant[b] | 50.0 |

[a]ESTOL EO3BW 3751, Unichema International
[b]DOW CORNING 200 Fluid, 350 cSt

Preferred coating compositions containing liquid flavors (A) and a mixture of liquid and encapsulated flavors (B) are shown in the following table.

| FLAVORED WAX COATING COMPOSITION | | |
|---|---|---|
| | Amount, wt. % | |
| Component | A | B |
| Polyethylene glycol ester of beeswax[a] | 38.5 | 30.5 |
| Silicone oil lubricant[b] | 25.0 | 25.0 |
| Mint flavor[c] | 34.0 | 26.0 |
| Spearmint cap.[d] | | 4.0 |
| Peppermint cap.[e] | | 12.0 |
| Saccharin | 0.5 | 0.5 |
| Ethanol, 96% | 2.0 | 2.0 |

[a]ESTOL EO3BW 3751, Unichema International
[b]DOW CORNING 200 Fluid, 350 cSt
[c]Noville Fragrance #62082

Alternatively, nylon solutions in lower alkanols of the types conventionally used in coating dental flosses can be used. An example is the GENTAL™ alkanolic nylon solutions (General Plastics Corporation, Bloomfield, N.J.). Polyurethanes which can be used include alcohol soluble urethane prepolymers sold under the tradename SPENLITE (Reichold Chemical) and water dispersible urethanes such as the anionic colloidal urethane elastomer dispersions sold under the tradename SPENSOL® polyurethane dispersions (Spencer-Kellog Products). Optimally, the coating solution or emulsion is a mixture of from 5 to 15 percent of alkanol-soluble nylon and from 5 to 15 percent water-dispersible polyurethane in a mixed water/alkanol solution such as a water/ethanol solution such as a mixture of 75 wt. % of GENTAL™ A151A alkanolic nylon solution and 25 wt % of SPENSOL® L54 aqueous polyurethane dispersion.

Figure 4:
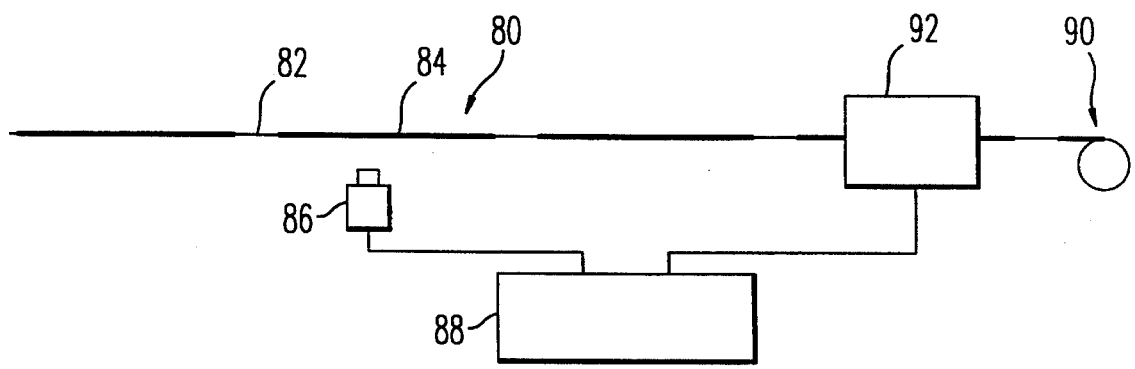
FIG. 4 is a schematic representation of the optical counter and spooler assembly for the process of this invention.

FIG. 4 is a schematic view of a counter, spooler and cutter apparatus for use in the process of this invention. The continuous length of yarn segments 80 comprises relatively non-stretching thread portions 82 and easily stretched brush portions 84. A conventional contrast scanner 86 is positioned to scan the yarn as it passes. The fluctuation in signal produced by the change in reflectance of the thread and brush sections is translated into counts by a conventional computerized counter assembly 88. The floss is collected on spool 90. When the counts total a predetermined number of segments, the cutter 92 is activated, precisely severing the floss into the desired length or number of segments. Optical scanning, counting and cutting components are described in U.S. Pat. No. 4,737,904, for example, the entire contents of which are hereby incorporated by reference.

Provided that a highly sensitive photodetector is used, the difference in reflectance between the thread and brush section materials can provide a count signal. However, a stronger signal is obtained if a section such as at least a portion of the thread section is marked with a high contrast dye, as described above. The preferred product of this process is a continuous floss brush product comprising a continuous length of floss segments having alternating portions of yarn sections which stretch under slight tension separated by thread sections which do not significantly stretch under tension, at least a portion of each thread section being marked with a dye.

Although preferred embodiments of the subject invention have been described in some detail, it is understood that obvious variations can be made without departing from the spirit and the scope of the invention as defined by the appended claims.

The invention claimed is:

1. A continuous process for manufacturing a continuous length of floss brush segments comprising the steps of
    a) applying a polymer solution at a repeated preselected distance interval to a continuous length of floss yarn and solidifying the polymer while the floss yarn is under tension to produce a continuous floss product of yarn sections which are expanded, separated by thinner thread sections having a polymer coating,
    b) treating the floss yarn to expand the yarn sections further to form brush sections,
    c) detecting the passage of a predetermined number of segments, comprising thread and brush sections, while the continuous floss brush is under substantially zero tension, using a detector, and
    d) cutting and packaging a length of the continuous floss brush containing the predetermined number of segments.

2. A continuous process of claim 1 which includes applying a polymer solution to at least the yarn sections once the polymer on the thread sections has solidified and before treating the floss yarn to expand the yarn sections.

3. A continuous process of claim 1 in which the detector is an optical detector.

4. A continuous process of claim 3 including applying a dye marker to at least a portion of the thread sections, whereby the accuracy of the optical detection of the thread sections of the continuous floss brush is increased.

5. A continuous process of claim 1 wherein the yarn is a nylon yarn, and the yarn sections are expanded by treatment with heat and water vapor when the yarn sections are under substantially zero tension, to yield a product with a highly expanded brush section which stretches under slight tension.

6. A continuous floss brush product comprising a continuous length of floss segments that, under zero tension, has alternating portions of yarn sections which are expanded, separated by thread sections having a diameter which is less than the diameter of relaxed uncoated yarn from which it was formed, either the yarns sections or the thread sections having at least a portion that is marked with a dye so as to form an alternating pattern of marked and unmarked sections.

7. A continuous floss brush product of claim 6 comprising a reverse twisted, high tenacity nylon yarn comprising at least two thread sections, the thread sections being separated by a floss brush section integral therewith of yarn having a diameter of 1 to 3 mm in its relaxed state, a diameter of at least 0.5 mm under a tension of 0.05N, the floss brush having a breaking strength of at least 5N.

8. A continuous floss brush product of claim 7 wherein the reverse twisted high tenacity nylon yarn has a breaking strength of at least 20N.

9. A dental floss brush of claim 7, wherein the thread sections have diameters, in their relaxed state, of less than 50 percent of the diameter of the relaxed, uncoated yarn from which they were formed.

10. A continuous floss brush product of claim 7 wherein each floss brush section has a diameter under a tension of 0.05N of at least 60 percent of relaxed uncoated yarn from which it was formed.

11. A continuous floss brush product of claim 6, wherein at least a portion of each of the thread sections is marked with a dye.

12. A continuous process for manufacturing a continuous length of floss brush segments comprising the steps of;
    a) applying a polymer solution at a repeated preselected distance interval to a continuous length of floss yarn and solidifying the polymer while the floss yarn is under tension to produce a continuous floss product of yarn sections which are expanded, separated by thinner thread sections having a polymer coating,
    b) treating the floss yarn to expand the yarn sections further to form brush sections, and c) applying a dye marker to at least a portion of either the thread sections or the yarn sections so as to form an alternating pattern of marked and unmarked section.

13. A continuous process of claim 12, wherein the dye marker is applied to at least a portion of each of the thread sections.

14. A continuous process of claim 12 which includes applying a polymer solution to at least the yarn sections once the polymer on the thread sections has solidified and before treating the floss yarn to expand the yarn sections.

15. A continuous process of claim 12, wherein the yarn is a nylon yarn, and the yarn sections are expanded by treatment with heat and water vapor when the yarn sections are under substantially zero tension, to yield a product with a highly expanded brush section which stretches under slight tension.

* * * * *